US006862479B1

(12) United States Patent
Whitehurst et al.

(10) Patent No.: US 6,862,479 B1
(45) Date of Patent: Mar. 1, 2005

(54) SPINAL CORD STIMULATION AS A THERAPY FOR SEXUAL DYSFUNCTION

(75) Inventors: Todd K. Whitehurst, Sherman Oaks, CA (US); James P. McGivern, Stevenson Ranch, CA (US)

(73) Assignee: Advanced Bionics Corporation, Valencia, CA (US)

(*) Notice: Subject to any disclaimer, the term of this patent is extended or adjusted under 35 U.S.C. 154(b) by 614 days.

(21) Appl. No.: 09/927,757

(22) Filed: Aug. 9, 2001

Related U.S. Application Data
(60) Provisional application No. 60/229,167, filed on Aug. 30, 2000.

(51) Int. Cl.[7] .................................................. A61N 1/32
(52) U.S. Cl. ...................... 607/39; 607/117; 604/891.1; 604/503; 604/522
(58) Field of Search ............................. 607/39, 117, 1, 607/2; 600/38, 41; 604/890.1, 891.1, 502, 522, 503

(56) References Cited

U.S. PATENT DOCUMENTS

| | | | |
|---|---|---|---|
| 3,941,136 A | 3/1976 | Bucalo | 128/422 |
| 4,542,753 A | 9/1985 | Brenman et al. | 128/788 |
| 4,585,005 A | 4/1986 | Lue et al. | 128/419 |
| 5,193,539 A | 3/1993 | Schulman et al. | 128/419 |
| 5,193,540 A | 3/1993 | Schulman et al. | 128/419 |
| 5,312,439 A | 5/1994 | Loeb | 607/2 |

(List continued on next page.)

FOREIGN PATENT DOCUMENTS

| | | |
|---|---|---|
| WO | 9837926 | 3/1998 |
| WO | 9843700 | 8/1998 |
| WO | 9843701 | 8/1998 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9 (Sep. 1997), pp. 781–790.

Lue, et al., "Electrostimulation and Penile Erection", Urol. Int. 40 (1985), pp. 60–64.

Martinez–Pineiro, et al., Rat Model for the Study of Penile Erection: Pharmacologic and Electrical–Stimulation Parameters, Eur Urol 25 (1994), pp. 62–70.

Shafik, A., "Extrapelvic Cavernous Nerve Stimulation in Erectile Dysfunction", Andrologia 28 (May–Jun. 1996), pp. 151–156.

(List continued on next page.)

Primary Examiner—Mark Bockelman
(74) Attorney, Agent, or Firm—Laura Haburay Bishop; Bryant R. Gold

(57) ABSTRACT

One or more implantable system control units (SCU) apply one or more stimulating drugs and/or electrical pulses to a spinal section responsible for innervating the male reproductive organs. The SCU uses a power source/storage device, such as a rechargeable battery. If necessary, periodic recharging of such a battery is accomplished, for example, by inductive coupling with an external appliance. The SCU provides means of stimulating a tissue(s) with electrical and/or infusion pulses when desired, without the need for external appliances during the stimulation session. When necessary, external appliances are used for the transmission of data to and/or from the SCU(s) and/or for the transmission of power. In a preferred embodiment, the system is capable of open- and closed-loop operation. In closed-loop operation, at least one implant includes a sensor, and the sensed condition is used to adjust stimulation parameters.

44 Claims, 6 Drawing Sheets

U.S. PATENT DOCUMENTS

| | | | |
|---|---|---|---|
| 5,439,938 A | 8/1995 | Snyder et al. | 514/565 |
| 5,454,840 A | 10/1995 | Krakovsky et al. | 607/39 |
| 5,571,118 A | 11/1996 | Boutos | 607/138 |
| 5,775,331 A | 7/1998 | Raymond et al. | 128/741 |
| 5,938,584 A | 8/1999 | Ardito et al. | 600/38 |
| 6,051,017 A | 4/2000 | Loeb et al. | 607/1 |
| 6,104,960 A * | 8/2000 | Duysens et al. | 607/117 |
| 6,169,924 B1 | 1/2001 | Meloy et al. | 607/39 |
| 6,650,943 B1 * | 11/2003 | Whitehurst et al. | 607/39 |
| 6,733,485 B1 * | 5/2004 | Whitehurst et al. | 604/500 |

OTHER PUBLICATIONS

Stief, et al., "The Influence of Anterior Root Stimulation (S2) in Deafferented Spinal Cord Injury Men on Cavernous Electrical Activity", The Journal of Urology 148 (Jul. 1992), pp. 107–110.

Tai, et al., "Penile Erection Produced by Microstimulation of the Sacral Spinal Cord of the Cat", IEEE Transactions Rehabilitation Engineering 6 (Dec. 1998) pp. 374–381.

Shafik A., "Perineal Nerve Stimulation: Role in Penile Erection", International Journal of Impotence Research. 9 (Mar. 1997), pp. 11–16.

Shafik A., "Cavernous Nerve Stimulation Through an Extrapelvic Subpubic Approach: Role in Penile Erection", Eur Urol 26 (1994), pp. 98–102.

Creasey GH., "Electrical Stimulation of Sacral Roots for Micturition After Spinal Cord Injury", Urologic Clinics of North America 20 (Aug. 1993), pp. 505–515.

AB–124U; Whitehurst and McGivern, inventors; U.S. Appl. No. 09/799,988, filed Mar. 6, 2001; entitled "Fully Implantable Neurostimulator for Cavernous Nerve Stimulation as a Therapy for Erectile Dysfunction and Other Sexual Dysfuntion".

* cited by examiner

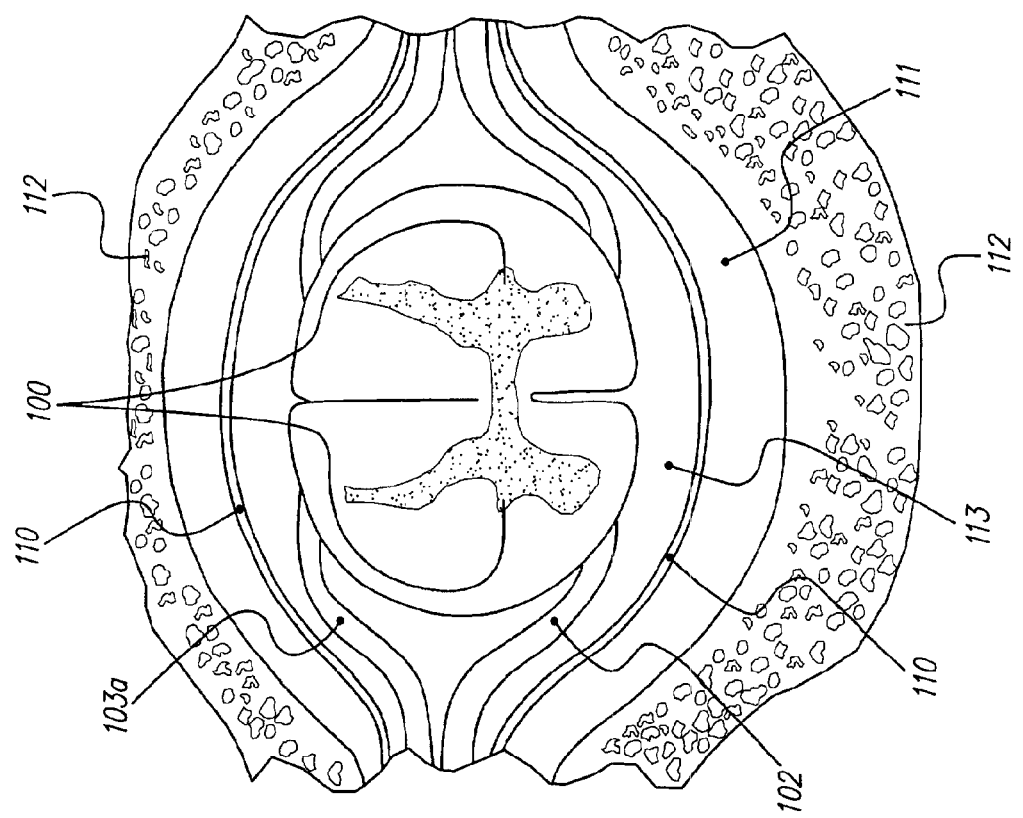

SPINAL CORD STIMULATION AS A THERAPY FOR SEXUAL DYSFUNCTION

The present application claims the benefit of U.S. Provisional Patent Application Ser. No. 60/229,167, filed Aug. 30, 2000, which application is incorporated herein by reference in its entirety.

FIELD OF THE INVENTION

The present invention generally relates to implantable drug delivery and stimulation systems, and more particularly relates to utilizing one or more implantable stimulators and/or drug infusion devices as a therapy for sexual dysfunction.

BACKGROUND OF THE INVENTION

Recent estimates suggest that the number of U.S. men with erectile dysfunction may be near 10 to 20 million, and inclusion of individuals with partial erectile dysfunction increases the estimate to about 30 million. The male erectile response is initiated by the action of neurons, or nerve cells (i.e., neuronal action), and maintained by a complex interplay between events involving blood vessels (i.e., vascular events) and events involving the nervous system (i.e., neurological events).

It is parasympathetic neuronal action that initiates the male erectile response. The cavernous nerves (designated greater and lesser) supply parasympathetic fibers to the corpora cavernosum and corpus spongiosum, the erectile tissue in the penis containing large interspaces capable of being distended with blood. The cavernous nerves arise from the spinal cord, and researchers have elucidated the location of the spinal cord neurons that ultimately give rise to the cavernous nerves.

In 1985, Lue labeled the cavernous nerves of dogs with horseradish peroxidase, which was transported in a retrograde fashion to the spinal cord nuclei cell bodies. The neurons thus labeled were mediolateral autonomic neurons at T12–L3 and S1–S3.

In a 1992 study of three male patients with complete spinal cord lesions (in the thoracic region), Stief found that spinal cord stimulation of the anterior (i.e., ventral) roots of S2 to 55 produced erection in all 3 patients. [Stief, et al., "The influence of anterior root stimulation (S2) in deafferented spinal cord injury men on cavernous electrical activity." Journal of Urology, 1992 July; 148(1):107–110.] Stief further indicated that, using a pulse amplitude of 30 volts and a pulse width of 400 μsec, stimulation frequencies of 12–30 Hz produced full erection, while 7–8 Hz and 45 Hz produced only partial erection. However, all three patients of this study received treatment for bladder spasticity, which included deafferentation (i.e., dorsal rhizotomy, or lesioning) of the dorsal (sensory) roots from S2 to 35, and implantation of U-shaped electrodes around the anterior roots of S2 to S5. These electrodes were implanted intradurally. In addition, the stimulator used (the Brindley stimulator) is strictly radio-frequency controlled.

An article by Creasey in 1993 entitled "Electrical stimulation of sacral roots for micturition after spinal cord injury" [Urol Clin North America, 1993 August; 20(3):505–515] focused on restoration of bladder function. Two stimulator systems were used: the Finetech implant (also known as the Brindley stimulator, as used in the Stief study) and the Medtronic implant. The article says "Erectile function is reported to be unaffected by the Medtronic implant." The Finetech implant did affect erectile function. However, as mentioned earlier, the Finetech system is strictly radio-frequency controlled, and is implanted "using an intradural approach to facilitate the separation of anterior from posterior roots." While the article mentions that "electrodes suitable for extradural implantation adjacent to the mixed sacral nerves" have been developed, the article does not appear to report on any use of such electrodes. With the Finetech implant, the "electrodes are placed around these [sacral anterior] roots . . . [and c]ables from the electrodes are brought out through a grommet in the dura, which is then closed." In addition, "[t]he procedure is usually combined with intradural division of the posterior roots of S2–S5." In other words, as with the Stief study, methods used in this study also included rhizotomy of afferents, e.g., posterior roots (a.k.a., dorsal roots), or rhizotomy of dorsal root ganglion or ganglia.

In a 1998 study of the sacral neural pathways mediating penile erection in the cat, Tai found that the greatest change in cavernous sinus pressure (CSP) was elicited by stimulation of the S1 ventral roots rather than the S2 or S3 spinal roots. [Tai, et al. "Penile erection produced by microstimulation of the sacral spinal cord of the cat." IEEE Trans Rehabil Eng, 1998 December; 6(4):374–381.] Tai further reported that, "Maximal CSP responses were evoked by microstimulation in the middle of the S1 ventral horn, 1.6–2.8 mm below the cord surface and midway between the midline and the lateral edge of the gray matter." The best responses were achieved with stimulus intensities of 50–150 μA, at a pulse width of 200 psec, and at frequencies of 30–40 Hz, and occurred after a delay of 8–40 seconds. However, as common defined by those of skill in the art, "microstimulation," as used by Tal, is provided by a fine-tipped "microelectrode" (Tai's had a surface area of 200–400 μm$^2$) producing very low amplitude currents, generally less than 200 μA (Tai used 50–150 μA). The other stimulation used by Tai was provided by a "hook electrode." No chronic, implantable stimulator was used. Tai used both the microelectrode and hook electrode to acutely stimulate the ventral roots intradurally.

Parasympathetic activity allows erection by relaxation of smooth muscle (i.e., muscle found in the walls of internal organs, blood vessels, hair follicles, etc. that contracts without voluntary control) and dilation of the helicine arteries, which are coiled arteries found in the erectile tissue of the penis. The dilation of the arteries causes greatly increased blood flow through the erectile tissue, which leads to expansion of the three cylinders of erectile tissue in the penis (i.e., the corpora cavernosum and the corpus spongiosum). As the corpora cavernosum and the corpus spongiosum expand, the venous structures draining the penis are compressed against the fascia surrounding each of the erectile tissues (i.e., the tunica albuginea of the corpora cavernosum and the tunica albuginea of the corpus spongiosum). Thus, the outflow of blood is restricted, and the internal pressure increases. This vein-obstruction process is referred to as the corporal veno-occlusive mechanism.

Conversely, constriction of the smooth muscle and helicine arteries induced by sympathetic innervation (i.e., stimulation by nerves) from the hypogastric nerves, for example, from certain nerves of the inferior hypogastric plexus, may make the penis flaccid.

Erectile dysfunction has a number of causes, both physiological and psychological, and in many patients the disorder may be multifactorial. The causes include several that are essentially neurologic in origin. Damage to the pathways used by the autonomic nervous system to innervate the penis may interrupt "psychogenic" erection initiated by the central nervous system. Psychogenic erection has a mental or emotional origin, rather than a physical basis. Lesions (e.g., injury, infection, or disease) of the somatic nervous pathways (i.e., any of the nerves associated with sensation or motion) may impair reflexogenic erections (i.e., involuntary, instinctive physiological response to a stimulus) and may interrupt tactile sensation needed to maintain psychogenic erections. Spinal cord lesions may produce varying degrees of erectile failure depending on the location and severity of the lesions.

Not only lesions affect erectile ability; disorders leading to peripheral neuropathy may also impair neuronal innervation of the penis. Peripheral neuropathy is a disorder or abnormality of the part of the nervous system constituting the nerves outside the central nervous system and including the cranial nerves, the spinal nerves, and the sympathetic and parasympathetic nervous systems. Peripheral neuropathy may also impair neuronal innervation of the sensory afferents—the nerves that conduct impulses from the periphery of the body to the brain or spinal cord, transmitting impulses from sense organs to nerve centers. Peripheral neuropathy is a potential sequela of a number of diseases, e.g., diabetes mellitus.

The endocrine system (glands such as the thyroid, adrenal, or pituitary, having hormonal secretions that pass directly into the bloodstream), particularly the production of androgens (steroid hormones, such as testosterone or androsterone, that control the development and maintenance of masculine characteristics), appears to play a role in regulating sexual interest, and may also play a role in erectile function.

In men of all ages, erectile failure may diminish willingness to initiate sexual relationships because of fear of inadequate sexual performance or rejection. Because males, especially older males, are particularly sensitive to the social support of intimate relationships, withdrawal from these relationships because of such fears may have a negative effect on their overall health.

Some forms of erectile dysfunction are treated with medication, with varying degrees of success. For instance, the well-publicized oral medication VIAGRA® (active ingredient sildenafil citrate) requires an hour to exert its full effects, and it may have significant side effects such as abnormal vision, flushing, headache, and diarrhea.

Intracavernosal injection therapy, in which a patient injects vasodilator substances (e.g., papaverine) into the corpora of the penis, suffers a high rate of patient dropout, as does the therapeutic application of vacuum constriction devices. Several forms of penile prostheses are available, including semirigid, malleable, and inflatable, but these have significant problems with mechanical failure, infection, and device erosion.

Various stimulation devices have been proposed for treating sexual dysfunction. Some devices stimulate through the skin, such as intrarectal stimulation devices. Other devices require significant surgical procedures for placement of electrodes, leads, and processing units. For instance, as discussed earlier, studies have used intradural implantation of electrodes, which can lead to complications such as cerebral spinal fluid leakage, increased risk of infection, among other things. As another example also discussed earlier, studies have included rhizotomy (i.e., lesioning) of Adorsal roots or other structures. Known devices may also require an external apparatus that needs to be strapped or otherwise affixed to the skin. While several patents exist regarding stimulators for treatment of erectile dysfunction, the inventors know of no chronic, fully implantable neurostimulator device that is commercially available.

BRIEF SUMMARY OF THE INVENTION

The invention disclosed and claimed herein provides means for treating sexual dysfunction by applying stimulation, via a stimulating device that applies either electrical stimulation and/or one or more stimulating drugs, to selected areas in or near the spinal cord. One or more electrodes are surgically implanted to provide electrical stimulation from an implantable signal/pulse generator (IPG) and/or one or more catheters are surgically implanted to infuse drug(s) from an implantable pump. Alternatively, a miniature implantable neurostimulator, such as a Bionic Neuron (also referred to as a BIONd microstimulator), may be implanted.

The electrical stimulation and/or stimulating drug(s) are preferably applied to one or more selected areas of the spinal cord, spinal ventral roots, and/or autonomic ganglia. Specifically, one or more electrodes and/or catheter discharge openings are preferably placed in or adjacent to the ventral (motor) horn(s), ventral root(s), sympathetic ganglia, and/or the mediolateral column of the spinal cord of one or more spinal segments T10–T12, L1–L5, and S1–S5. Stimulation may be applied through the dura, with electrodes and/or catheter discharge openings implanted in the epidural space, and/or stimulation may be applied while the dorsal and ventral roots are intact (i.e., no rhizotomy is necessary).

According to one embodiment of the invention, the stimulation increases excitement of the parasympathetic input to the penis; relatively low-frequency electrical stimulation of parasympathetic fibers is likely to produce such excitement. According to another embodiment of the invention, the stimulation decreases excitement of the sympathetic input to the penis; relatively high-frequency electrical stimulation of sympathetic fibers is likely to produce such inhibition. Additional embodiments provide stimulation with drugs to, e.g., inhibit sympathetic input that interferes with erection.

Stimulation (electrical or with a drug(s)) may be applied either interrmittently or continuously. Specific stimulation parameters may provide therapeutic advantages for various forms of sexual dysfunction. Additional uses include applications to emission (discharge of semen) and ejaculation (ejection of semen in orgasm). A single device may be implanted, or two or more devices may be implanted to achieve greater stimulation of all targeted nerves and other tissues.

The devices used with the present invention preferably possess one or more of the following properties:

at least two electrodes for applying stimulating current to surrounding tissue and/or at least one catheter for applying stimulating drug(s) to surrounding tissue;

electronic and/or mechanical components encapsulated in a hermetic package made from biocompatible material(s);

an electrical coil inside the package that receives power and/or data by inductive or radio-frequency (RF) coupling to a transmitting coil placed outside the body;

means for receiving and/or transmitting signals via telemetry; and means for receiving and/or storing electrical power within the package.

A stimulating device may operate independently, or in a coordinated manner with other implanted devices, or with external devices. In addition, a stimulating device may incorporate means for sensing sexual dysfunction, which it may then use to control stimulation parameters in a closed loop manner. According to one embodiment of the invention, the sensing and stimulating means are incorporated into a single device. According to another embodiment of the invention, a sensing means communicates sensed information to at least one device with stimulating means.

Thus, the present invention provides a therapy for sexual dysfunction that utilizes a stimulating device to apply either electrical stimulation and/or one or more stimulating drugs to one or more selected areas in and/or near the spinal cord. Other advantages of the present invention include, inter alia, the system's monitoring and programming capabilities, the power source, storage, and transfer mechanisms, the activation of the device by the patient or clinician, the system's open and closed-loop capabilities and closed-loop capabilities coupled with sensing a need for and/or response to treatment, coordinated use of one or more devices, and the compact size of the device(s).

BRIEF DESCRIPTION OF THE DRAWINGS

The above and other aspects, features, and advantages of the present invention will be more apparent from the following more particular description thereof, presented in conjunction with the following drawings wherein:

FIG. 2B is a superior view of the spinal cord and surrounding structures.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
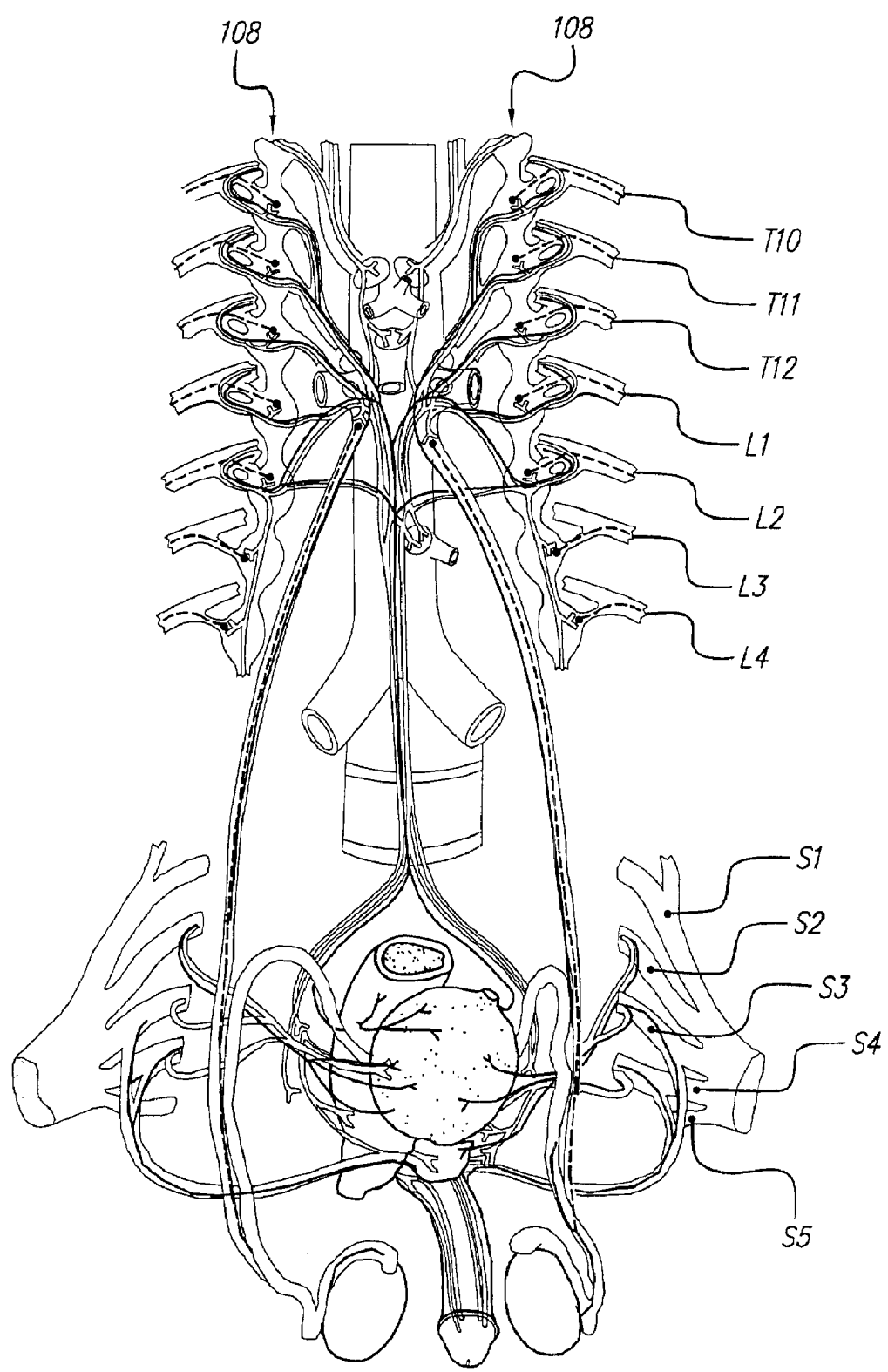
FIG. 1 illustrates the innervation of the male reproductive organs.

FIG. 1 is a schematic representation of the innervation of the male reproductive organs. Parasympathetic input from the autonomic nervous system initiates the male erectile response. Parasympathetic signals travel from the spinal cord (specifically, from the sacral nerves, especially the first, second, third, and fourth sacral nerves-S1, S2, S3, and S4, respectively), through the pelvic splanchnic nerves to the nerves of the penis.

Sympathetic input from the autonomic nervous system inhibits the erectile response. Sympathetic signals travel from the spinal cord (from thoracic nerves T10–T12 and lumbar nerves L1–L4, especially T12, L1, L2, and L3), through various splanchnic and hypogastric nerves to the nerves of the penis.

Figure 2A:
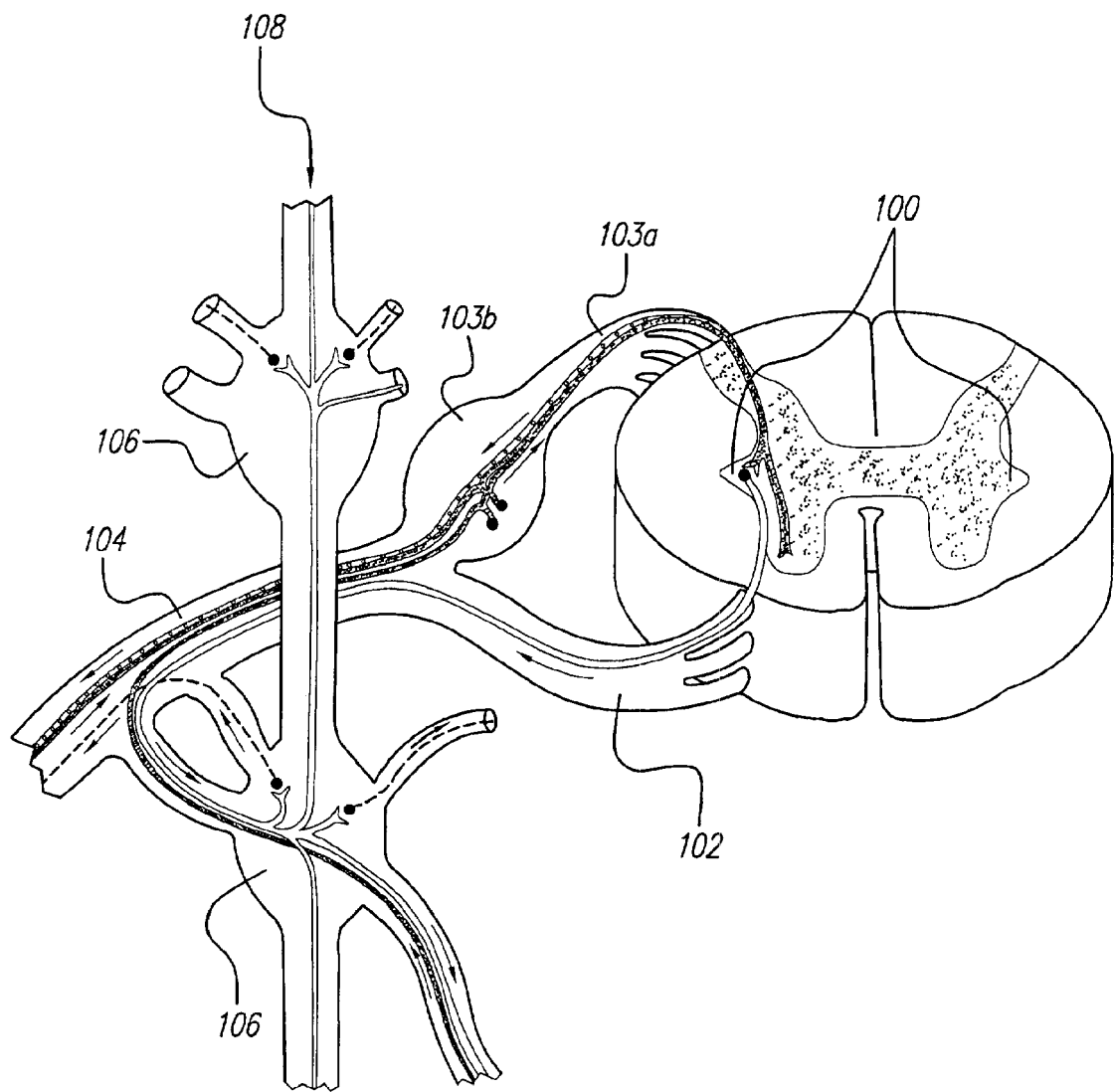
FIG. 2A depicts a section of the spinal cord and its autonomic pathways.

FIG. 2A depicts the autonomic pathways of an exemplary section of the spinal cord. The mediolateral nudeus 100 (also called the intermediolateral nucleus) is the cell column that forms the lateral horn of the gray matter of the spinal cord. The mediolateral nucleus extends from the first thoracic through the second lumbar segment and contains the autonomic motor neurons that give rise to the preganglionic fibers of the sympathetic system. Sympathetic signals travel from the mediolateral nucleus 100 through ventral (anterior) root 102 and spinal nerve 104 to a vertebral ganglion 106 of the sympathetic trunk 108. The sympathetic trunks extend from the base of the skull to the coccyx along either side of the spinal column. Dorsal (posterior) root 103*a* and dorsal root ganglion 103*b* carry somatic (sensory) information between the spinal cord and the spinal nerve 104.

FIG. 2B is a superior view of the spinal cord and surrounding structures, such as the dura mater 110. The dura mater, which is also referred to as the dura, is a tough, fibrous membrane that envelops the brain and spinal cord. In the spinal cord, the dura 110 is separated from the vertebra 112 by a considerable space, commonly called the epidural space 111. The space between the dura 110 and the spinal cord is commonly referred to as the subdural or intradural space 113.

Figure 3:
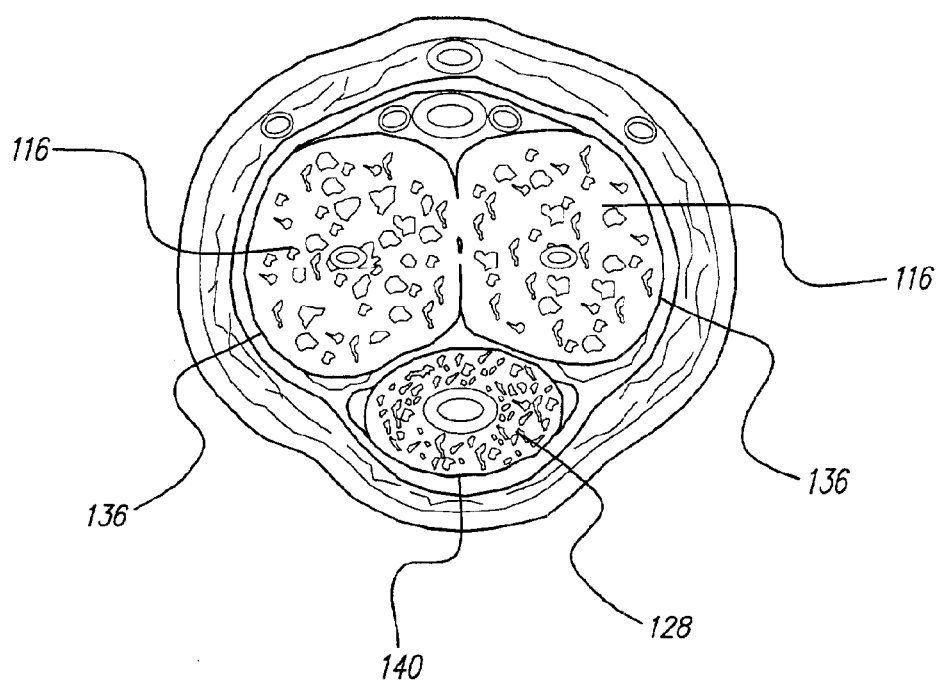
FIG. 3 is a section view through the body of a penis.

Referring next to FIG. 3, the parasympathetic signals that initiate erection are carried to the nerves of the penis, which innervate the corpora cavernosum 116 and corpus spongiosum 128, causing relaxation of smooth muscle surrounding the arteries and arterioles of the penis and dilation of the arteries and arterioles of the penis. Sympathetic innervation prevents this relaxation of the smooth muscle, and thus prevents erection. The dilation of the arteries and arterioles causes increased blood flow through the erectile tissue, which leads to expansion of the corpora cavernosum 116 and the corpus spongiosum 128. Due to this expansion, the venous structures draining the penis are compressed against the corpora cavernosum's tunica albuginea 136 and the corpus spongiosum's tunica albuginea 140. Thus, the outflow of blood is restricted, and the internal pressure increases.

To treat sexual dysfunction in accordance with the teachings of the present invention, stimulation is provided via electrical stimulation and/or one or more drugs. In one preferred alternative, an implantable signal generator and electrode(s) and/or an implantable pump and catheter(s) are used to deliver electrical stimulation and/or one or more stimulating drugs to specific areas in or near the spinal cord. One or more electrodes are surgically implanted in or near the spinal cord to provide electrical stimulation, and/or one or more catheters are surgically implanted in or near the spinal cord to infuse the drug(s).

In another preferred embodiment, electrical stimulation is provided by one or more small neurostimulator(s) 150, referred to herein as microstimulators. The microstimulators of the present invention are preferably of the type referred to as BION® devices. The following documents describe various features and details associated with the manufacture, operation, and use of BION implantable microstimulators, and are all incorporated herein by reference:

| Application/Patent/ Publication No. | Filing/ Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| PCT Publication WO 98/37926 | published Sep. 3, 1998 | Battery-Powered Patient Implantable Device |
| PCT Publication WO 98/43700 | published Oct. 8, 1998 | System of Implantable Devices For Monitoring and/or Affecting Body Parameters |
| PCT Publication WO 98/43701 | published Oct. 8, 1998 | System of Implantable Devices For Monitoring and/or Affecting Body Parameters |
| U.S. Pat. No. 6,051,017 (App. 09/077, 662) | Issued Apr. 18, 2000 published September 1997 | Improved Implantable Microstimulator and Systems Employing Same Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 4:
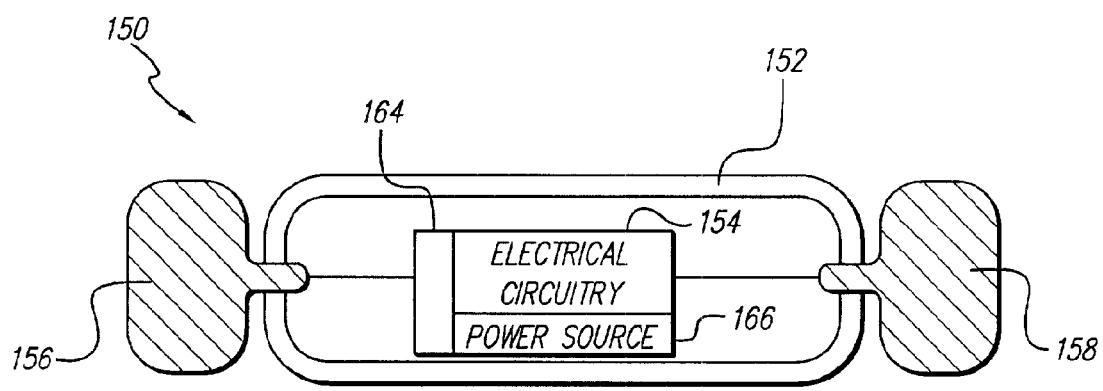
FIG. 4 illustrates an exemplary embodiment of a stimulation system of the present invention.

As shown in FIG. 4, microstimulator 150 includes a narrow, elongated capsule 152 containing electronic circuitry 154 connected to electrodes 156 and 158, which pass through the walls of the capsule at either end. As detailed in the referenced patents, electrodes 156 and 158 comprise a stimulating electrode (to be placed close to the target tissue) and an indifferent electrode (for completing the circuit). Other configurations of microstimulator device 150 are possible, as is evident from the above-referenced patents.

Advantageously, implantable microstimulator 150 is sufficiently small to permit its placement in or adjacent to the structures to be stimulated. As used herein, "adjacent" means as close as reasonably possible to the target tissue(s), including touching or within the targeted tissue(s), but in general, may be as far as about 150 mm from the target tissue(s).

Capsule 152 preferably has a diameter no greater than about 4–5 mm, more preferably only about 3.5 mm, and most preferably less than 3.5 mm. Capsule length is preferably no greater than about 30–40 mm, more preferably only about 20–30 mm, and most preferably less than 20 mm. The shape of the microstimulator is preferably determined by the structure of the desired target, the surrounding area, and the method of surgical insertion. A thin, elongated cylinder with electrodes at the ends, as shown in FIG. 4, is currently preferred, but other shapes, such as disks or helical structures, are possible.

Microstimulator 150, when used, is preferably implanted with a surgical insertion tool specially designed for the purpose, or is injected (e.g., via a hypodermic needle). Alternatively, microstimulator device 150 may be implanted via conventional surgical methods, or may be inserted using other endoscopic or laparoscopic techniques. A more complicated surgical procedure may be required for purposes of fixing the microstimulator in place.

The external surfaces of microstimulator device 150 are advantageously composed of biocompatible materials. Capsule 152 is preferably made of glass or ceramic to provide a hermetic package that will exclude water vapor but permit passage of electromagnetic fields used to transmit data and/or power. Electrodes 156 and 158 are preferably made of a noble or refractory metal, such as platinum, iridium, tantalum, titanium, niobium or their alloys, in order to avoid corrosion or electrolysis which could damage the surrounding tissues and the device.

In one preferred embodiment of the instant invention, microstimulator 150 comprises two, leadless electrodes. However, either or both electrodes 156 and 158 may alternatively be located at the ends of short, flexible leads as described in U.S. patent application Ser. No. 09/624,130, filed Jul. 24, 2000, which is incorporated herein by reference in its entirety. The use of such leads permits electrical stimulation to be directed more locally to a specific nerve, nerve branch, or other tissue a short distance from the surgical fixation of the bulk of the implantable microstimulator 150, while allowing most elements of microstimulator 150 to be located in a more surgically convenient site. This minimizes the distance traversed and the surgical planes crossed by the device and any lead(s). In a preferred embodiment, the leads are no longer than about 150 mm.

As mentioned earlier, stimulation is provided in accordance with the teachings of the present invention by electrical stimulation and/or one or more drugs. According to another preferred alternative, an implantable signal generator and electrode(s) and/or an Implantable pump and catheter(s) are used to deliver electrical stimulation and/or one or more stimulating drugs to specific areas in or near the spinal cord. One or more electrodes are surgically implanted in or near the spinal cord to provide electrical stimulation, and/or one or more catheters are surgically implanted in or near the spinal cord to infuse the drug(s).

The invention includes one or more system control units (SCU), which is preferably an implantable pulse/signal generator (IPG) in the case of electrical stimulation only, and is preferably an implantable pump in the case of drug infusion only. In cases requiring both electrical stimulation and drug infusion, one or more SCUs are used. Alternatively and preferably, an SCU provides both electrical stimulation and one or more stimulating drugs.

An SCU is preferably (but not necessarily) implanted in a surgically-created shallow depression or opening in the abdomen or above the buttock. An SCU preferably conforms to the profile of surrounding tissue(s) and/or bone(s), and is small and compact. This is preferable so that no unnecessary pressure is applied to the skin, as this may result in skin erosion or infection. An SCU has a diameter of preferably no greater than 75 mm, more preferably no greater than 65 mm, and most preferably about 45–55 mm. SCU thickness of approximately 10 mm is preferred, while a thickness of about 8 mm or less is more preferred.

In some preferred embodiments, one or more electrode leads 170 and/or catheters 180 attached to SCU 160 run in a surgically-created shallow groove(s) or channel(s) subcutaneously or in a fascial plane(s), to an opening(s) in the spinal column, and pass through the opening(s) into or onto the epidural space 111 and surrounding tissue. Placement of the electrodes and/or catheter discharge portion in epidural space avoids complications attendant with intradural or subdural placement, e.g., cerebral spinal fluid leakage and increased risk of infection, among other things. Recessed placement of the SCU and the lead(s) and/or catheter(s) has the advantages of decreased likelihood of erosion of the overlying skin, and of minimal cosmetic impact.

In the case of treatment with electrical stimulation, electrode(s) 172 are carried on lead 170 having a proximal end coupled to SCU 160. The lead contains wires electrically connecting electrodes 172 to SCU 160. SCU 160 contains electronic circuitry 154 that produces electrical stimulation pulses that travel through the wires of lead 170 and are delivered to electrodes 172, and thus to the tissue surrounding electrodes 172. To protect the electrical components inside SCU 160, the case of the SCU is preferably hermetically sealed. For additional protection against, e.g. impact, the case is preferably made of metal (e.g. titanium) or ceramic, which materials are also, advantageously, biocompatible. In addition, SCU 160 is preferably Magnetic Resonance Imaging (MRI) compatible.

In one alternative, the electrical stimulation may be provided as described in copending International Application Serial Number PCT/US00/20294, filed Jul. 26, 2000, which application is incorporated herein by reference in its entirety. The '010 application is directed to a "Rechargeable Spinal Cord Stimulator System" and is included by reference herein in its entirety.

In the case of treatment alternatively or additionally constituting drug infusion, catheter(s) 180 are coupled at a proximal end to SCU 160, which contains at least one pump 162 for storing and dispensing one or more therapeutic drug(s) through the catheter(s) 180. At a distal end, catheter 180 has a discharge portion 182 for infusing therapeutic dosages of the one or more drugs into a predetermined site in or near the spinal cord.

Figure 5:
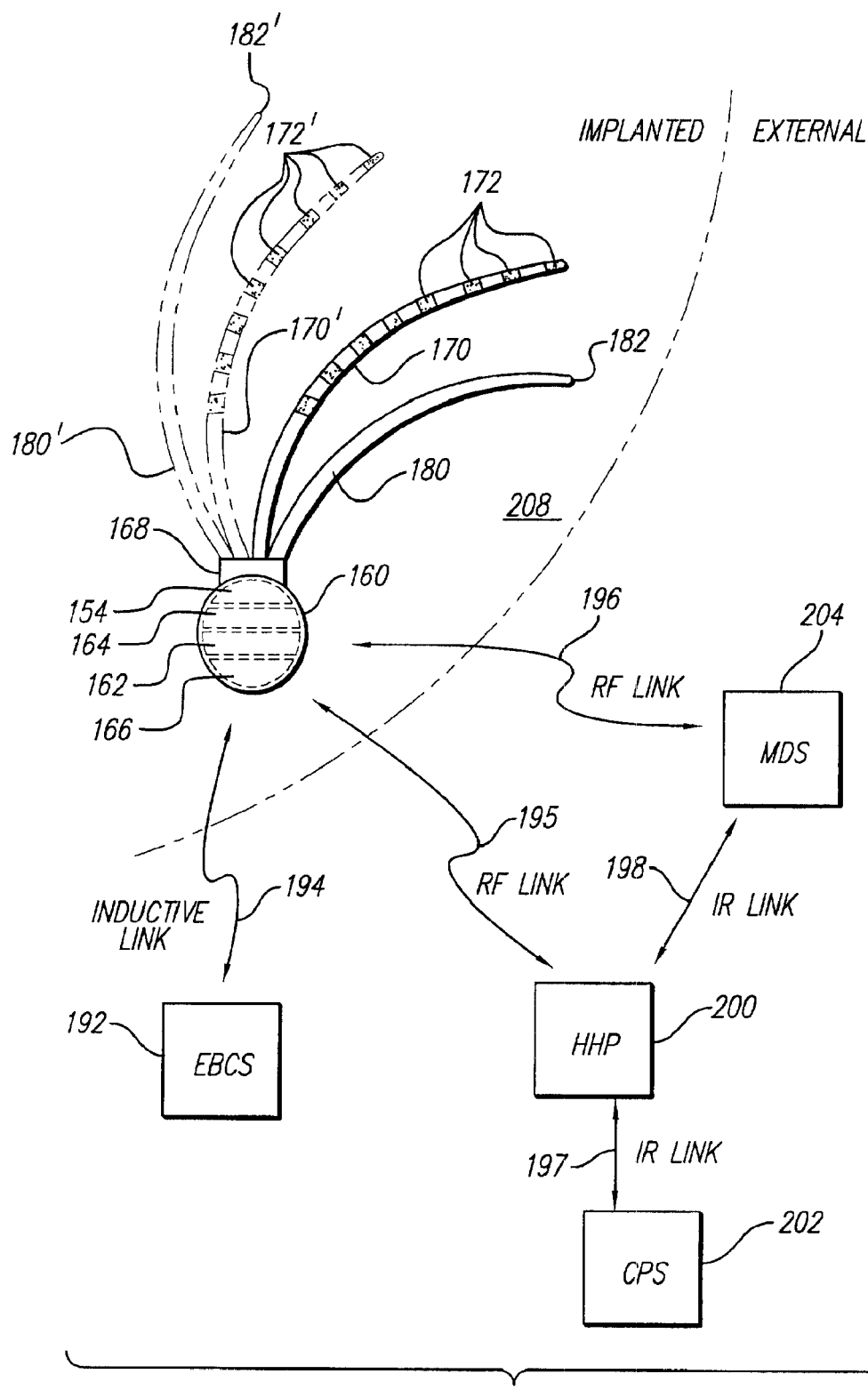
FIG. 5 illustrates another exemplary embodiment of a stimulation system of the present invention and of external components of the invention.

According to one preferred embodiment of the invention, and as depicted in FIG. 5, at least one lead 170 and/or catheter 180 is attached to SCU 160, via a suitable connector 168, if necessary. Each lead includes at least two electrodes 172, and may include as many as sixteen or more electrodes 172. Additional leads 170' and/or catheter(s) 180' may be attached to SCU 160. Hence, FIG. 5 shows (in phantom lines) a second catheter 180', and a second lead 170', having electrodes 172' thereon, also attached to the SCU 160.

Lead(s) 170 are preferably less than 5 mm in diameter, and more preferably less than 1.5 mm in diameter. Electrodes 172 are preferably arranged as an array, more preferably are at least two collinear electrodes, and more preferably at least 4 collinear electrodes. Electrodes 172, 172' are preferably made of a noble or refractory metal or compound, such as platinum, iridium, tantalum, titanium, titanium nitride, niobium, or alloys of any of these, in order to avoid corrosion or electrolysis which could damage the surrounding tissues and/or the device. SCU 160 is preferably programmable to produce either monopolar electrical stimulation, e.g., using the SCU case as an indifferent electrode, or bipolar electrical stimulation, e.g., using one of the electrodes of the electrode array as an indifferent electrode. A preferred SCU 160 has at least four channels and drives up to sixteen electrodes or more.

SCU 160 (which herein refers to implantable pump stimulators, IPG stimulators, IPG/pump combination stimulators, BION microstmulators, and/or other alternative devices known in the art) preferably contains electronic circuitry 154 for receiving data and/or power from outside the body by Inductive, radio-frequency (RF), or other electromagnetic coupling. In a preferred embodiment, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components that may be required to complete the electronic circuit functions, e.g. capacitor(s), resistor(s), coil(s), and the like. Electronic circuitry 154 dictates, for instance, the amplitude and duration of the electrical current pulse, when electrical stimulation is used.

SCU 160 also advantageously includes a programmable memory 164 for storing set(s) of data, stimulation, and control parameters. This feature allows electrical stimulation and/or drug stimulation and control parameters to be adjusted to settings that are safe and efficacious with minimal discomfort for each individual. Specific parameters provide therapeutic advantages for various forms of sexual dysfunction. For instance, some patients may respond favorably to intermittent stimulation, while others may require continuous treatment for relief. Electrical and drug stimulation parameters are preferably controlled independently. However, in some instances, they are advantageously coupled, e.g., electrical stimulation may be programmed to occur only during drug infusion.

In addition, stimulation and control parameters may be chosen to target specific neural populations and to exclude others, or to increase neural activity in specific neural populations and to decrease neural activity In others. For example, relatively low frequency neurostimulation (i.e., less than about 50–100 Hz) typically has an excitatory effect on surrounding neural tissue, leading to increased neural activity, whereas relatively high frequency neurostimulation (i.e., greater than about 50–100 Hz) typically has an inhibitory effect, leading to decreased neural activity. In addition, large diameter fibers (e.g., A-α and A-β fibers) respond to relatively lower current density stimulation compared with small diameter fibers (e.g., A-δ and C fibers). Furthermore, excitatory neurotransmitter agonists, such as adrenergic receptor agonists (e.g., norepinephrine), generally have an excitatory effect. Inhibitory neurotransmitter antagonists, such as gamma-aminobutyric acid (GABA) antagonists (e.g., bicuculline), also have an excitatory effect. Inhibitory neurotransmitter agonists, such as GABA agonists (e.g., diazepam), generally have an inhibitory effect. Excitatory neurotransmitter antagonists, such as adrenergic receptor antagonists (e.g., yohimbine) also have an inhibitory effect.

The preferred SCU 160 also includes a power source and/or power storage device 166. Possible power options for a stimulation device of the present invention, described in more detail below, include but are not limited to an external power source coupled to the stimulation device, e.g., via an RF link, a self-contained power source utilizing any means of generation or storage of energy (e.g., a primary battery, a replenishable or rechargeable battery such as a lithium ion battery, an electrolytic capacitor, or a super- or ultra-capacitor), and if the self-contained power source is replenishable or rechargeable, means of replenishing or recharging the power source (e.g., an RF link).

In one preferred embodiment and as depicted in FIG. 5, SCU 160 includes a rechargeable battery as a power source/storage device 166. The battery is recharged, as required, from an external battery charging system (EBCS) 192, typically through an inductive link 194. In this embodiment, SCU 160 includes a processor and other electronic circuitry 154 that allow it to generate electrical and/or infusion pulses that are applied to a patient 208 through electrodes 172 and/or catheter(s) 180 in accordance with a program stored in programmable memory 164.

According to one embodiment of the invention, an SCU operates independently. According to another embodiment of the Invention, an SCU operates in a coordinated manner with other SCU(s), other Implanted device(s), or other device(s) external to the patient's body. For instance, an SCU may control or operate under the control of another implanted SCU(s), other implanted device(s), or other device(s) external to the patient's body. An SCU may communicate with other implanted SCUs, other implanted devices, and/or devices external to a patient's body via, e.g., an RF link, an ultrasonic link, or an optical link. Specifically, an SCU may communicate with an external remote control (e.g., patient and/or physician programmer) that is capable of sending commands and/or data to an SCU and that is preferably capable of receiving commands and/or data from an SCU.

For example, in one preferred embodiment, SCU 160 of the present invention is activated and deactivated, programmed and tested through a hand held programmer (HHP) 200 (which may also be referred to as a patient programmer and is preferably, but not necessarily, hand held), a clinician programming system (CPS) 202 (which may also be hand held), or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for these purposes. Through these links, CPS 202, for example, may be coupled through HHP 200 to SCU 160 for programming or diagnostic purposes. MDS 204 may also be coupled to SCU 160, either directly through RF link 196, or indirectly through IR link 198, HHP 200, and RF link 195.

Figure 6:
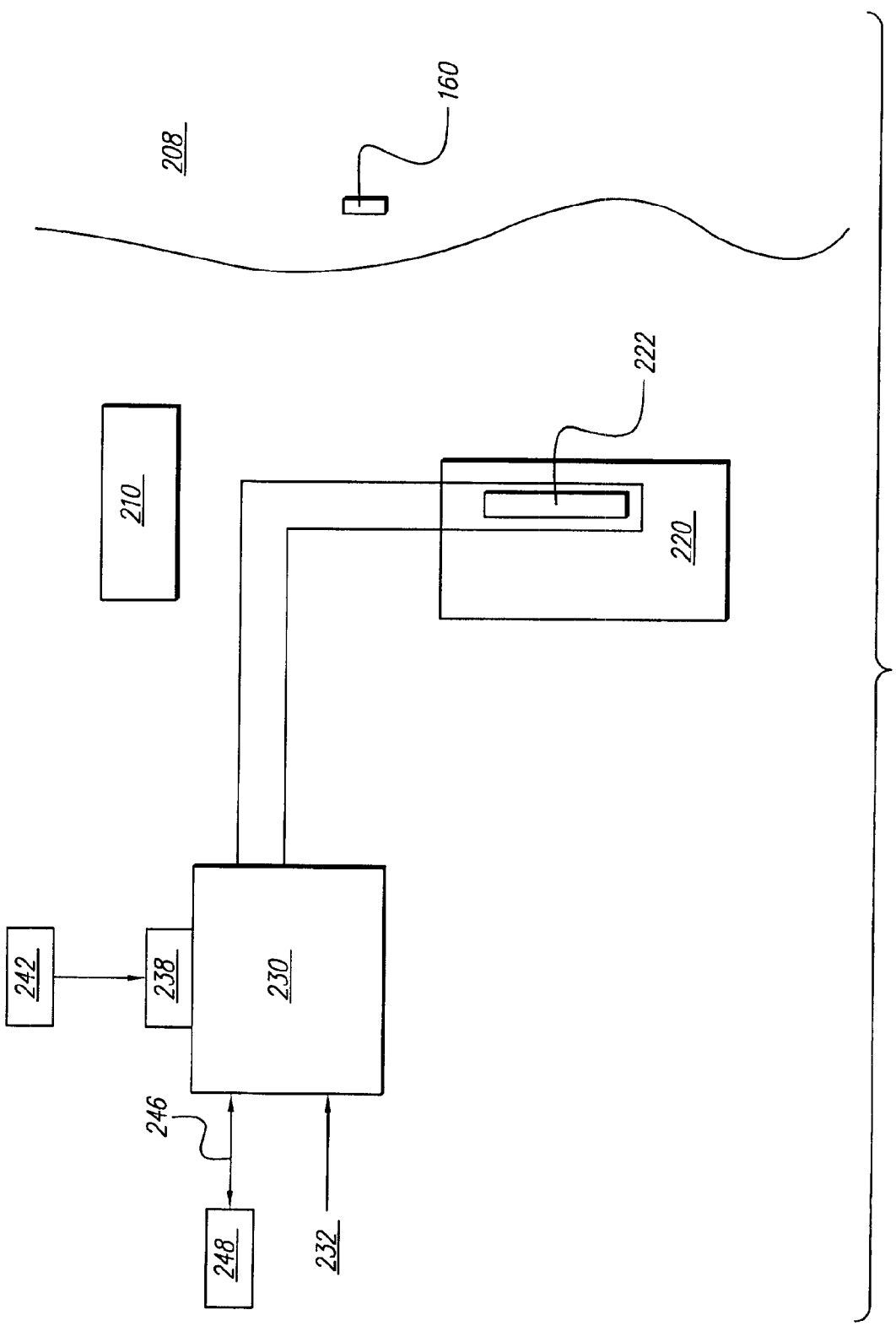
FIG. 6 illustrates additional exemplary embodiments of external components of the invention.

In another preferred embodiment, using for example, a BION® microstimulator(s) as described in the above referenced patents, and as illustrated in FIG. 6, the patient 208 switches SCU 160 on and off by use of controller 210, which is preferably handheld. Controller 210 operates to control SCU 160 by any of various means, including stimulator 160 sensing the proximity of a permanent magnet located in controller 210, or sensing RF transmissions from controller 210.

External components for another preferred embodiment related to programming and providing power to SCU 160 are also illustrated in FIG. 6. When it is required to communicate with SCU 160, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which receives power 232 from a conventional power source. External appliance 230 contains manual input means 238, e.g., a keypad, whereby the patient 208 or a caregiver 242 may request changes in the parameters of the electrical and/or drug stimulation produced during the normal operation of SCU 160. In this preferred embodiment, manual input means 238 preferably includes various electromechanical switches and visual display devices that provide the patient and/or caregiver with information about the status and prior programming of SCU 160.

Alternatively or additionally, external electronic appliance 230 is preferably provided with an electronic interface means 246 for interacting with other computing means 248, such as by a serial interface cable or infrared link to a personal computer or to a telephone modem. Such interface means 246 thus permits a clinician to monitor the status of the implant and prescribe new stimulation parameters from a remote location.

One or more of the external appliance(s) may advantageously be embedded in a cushion, pillow, mattress cover, or garment. Other possibilities exist, including a belt or other structure that may be affixed to the patient's body or clothing.

In order to help determine the strength and/or duration of electrical stimulation and/or the amount and/or type(s) of stimulating drugs required to produce the desired therapeutic effect, in one preferred embodiment, a patient's response to and/or need for treatment is sensed. For example, impedance, pressure (e.g. penile arterial pressure), penile blood flow (e.g., by direct flow sensor or by indirect means such as Doppler ultrasound), joint angle, muscle activity (e.g., EMG), nerve activity (e.g., ENG), electrical activity of the brain (e.g., EEG), or other activity is recorded in response to electrical and/or drug stimulation from SCU 160.

When electrodes of SCU 160 are implanted, for example, adjacent to spinal nerve 104, a stimulating electrode (or a separate electrode) of SCU 160 preferably senses changes in neural activity (e.g., via ENG) resulting from the stimulation applied to spinal nerve 104. Alternatively, an "SCU" dedicated to sensory processes communicates with an SCU that provides the electrical and/or infusion pulses. The implant circuitry 154 amplifies and transmits these sensed signals, which may be digital or analog.

Other methods of determining the required electrical and/or drug stimulation include observing the stimulation required to initiate erection, measuring neurotransmitter levels and/or their associated breakdown product levels, measuring medication levels, measuring hormone levels, as well as other methods mentioned herein, and yet others that will be evident to those of skill in the art upon review of the present disclosure. The sensed information Is preferably used to control the electrical and/or drug stimulation parameters of the SCU in a closed-loop manner.

For instance, in one embodiment of the present invention, a first and second "SCU" are provided. The second "SCU" periodically (e.g. once per minute) records penile arterial pressure and transmits it to the first SCU. The first SCU uses the sensed information to adjust stimulation parameters according to an algorithm programmed, e.g., by a physician. For example, the amplitude of electrical stimulation may be increased in response to decreased pressure. More preferably, one SCU performs both the sensing and stimulating functions.

While an SCU 160 may also incorporate means of sensing sexual dysfunction, e.g., via a joint angle sensor or electromyograph, it may alternatively or additionally be desirable to use a separate or specialized implantable device to record and telemeter physiological conditions/responses in order to adjust electrical and/or drug stimulation parameters. This information may be transmitted to an external device, such as external appliance 220, or may be transmitted directly to implanted SCU(s) 160. However, In some cases, it may not be necessary or desirable to include a sensing function or device, in which case stimulation parameters are determined and refined, for instance, by patient feedback.

Thus, it is seen that in accordance with some embodiments of the present invention (e.g., in FIG. 6), one or more external appliances are preferably provided to interact with SCU 160 to accomplish one or more of the following functions:

Function 1: If necessary, transmit electrical power from the external electronic appliance 230 via appliance 220 to SCU 160 in order to power the device and/or recharge the power source/storage device 166. External electronic appliance 230 may include an automatic algorithm that adjusts electrical and/or drug stimulation parameters automatically whenever the SCU(s) 160 is/are recharged.

Function 2: Transmit data from the external appliance 230 via the external appliance 220 to SCU 160 in order to change the operational parameters (e.g., electrical stimulation and/ or drug infusion parameters) produced by SCU 160.

Function 3: Transmit sensed data indicating a need for treatment or in response to stimulation from SCU 160 (e.g., impedance, pressure, joint angle, penile blood flow, muscle activity, nerve activity, electrical activity of the brain, neurotransmitter levels, levels of neurotransmitter breakdown products, medication levels, hormone levels, or other activity) to external appliance 230 via external appliance 220.

Function 4: Transmit data indicating state of SCU 160 (e.g., battery level, drug level, electrical stimulation and/or infusion settings, etc.) to external appliance 230 via external appliance 220.

By way of example, and still referring to FIG. 6, a treatment modality for erectile dysfunction may be carried out according to the following procedures:

1. An SCU 160 is implanted so that its electrodes 172 and/or catheter discharge portion 182 are located in or adjacent to ganglion 106 of sympathetic trunk 108. If necessary or desired, additional leads 170' and/or catheters 180' may be used so that, for example, electrodes 172' and/or catheter discharge portion(s) 182' may additionally or alternatively be located in or adjacent to ventral (anterior) root(s) 102 of S2 and/or S3 and/or S4. Preferably, dorsal (anterior) roots and ganglia 103a, 103b are left intact.

2. Using Function 2 described above (i.e., transmitting data) of external electronic appliance 230 and external appliance 220, SCU 160 is commanded to produce a series of inhibitory electrical stimulation pulses with gradually increasing amplitude up to no greater than 12 mA, possibly while infusing gradually increasing amounts of a sympathetic excitatory neurotransmitter antagonists, e.g., an antladrenergic medication, such as yohimbine, to the electrodes 172 and catheter discharge portions 182 located in or adjacent to ganglion 106 of sympathetic trunk 108. While thus causing inhibition of sympathetic pathways to the penis, electrodes 172' and/or catheter discharge portion 182' may additionally or alternatively apply excitatory stimulation to the parasympathetic ventral root(s) 102 of S2, S3, and/or S4.

3. After each electrical/infusion pulse, or brief series of stimulation pulses, or at some other predefined interval, any change in neural activity resulting from the applied stimulation is sensed, preferably by one or more electrodes 172 and/or 172' acting as sensors. If necessary, these responses are converted to data and telemetered out to external electronic appliance 230 via Function 3.

4. From the response data received at external appliance 230, the stimulus threshold for obtaining a response is determined and is used by a clinician 242 acting directly 238 or by other computing means 248 to transmit the desired electrical and/or drug stimulation parameters to SCU 160 in accordance with Function 2. Alternatively and preferably, external appliance makes the proper adjustments automatically, and transmits the proper stimulation parameters to SCU 160. Alternatively and most preferably, SCU 160 adjusts stimulation parameters automatically based on the sensed response.

5. When patient 208 desires to invoke electrical and/or drug stimulation to instigate erection, patient 208 employs controller 210 to set SCU 160 in a state where it delivers a prescribed stimulation pattern from a predetermined range of allowable stimulation patterns.

6. To cease electrical and/or drug stimulation (e.g., to allow the penis to return to a flaccid state), patient 208 employs controller 210 to turn off SCU 160.

7. Periodically, the patient or caregiver recharges the power source/storage device 166 of SCU 160, if necessary, in accordance with Function 1 described above (i.e., transmit electrical power).

As another example, a treatment modality for erectile dysfunction may be carried out according to the following procedures:

1. An SCU 160, such as an IPG/lead/electrode system or a microstimulator, e.g., a BION, is implanted so one or more electrodes are located in or adjacent to ventral root(s) 102 of S2. If necessary or desired, additional electrodes may be located in or adjacent to ventral root(s) 102 of S3 and/or S4. Preferably, dorsal (anterior) roots and ganglia 103a, 103b are left intact.

2. Using Function 2 described above (i.e., transmitting data) of external electronic appliance 230 and external appliance 220, SCU 160 is commanded to produce a series of excitatory electrical stimulation pulses, possibly with gradually increasing amplitude up to no greater than 12 mA.

3. Any change in neural activity is sensed, as described above.

4. The stimulus threshold for obtaining a response is determined, as described earlier.

5. As described above, patient 208 employs controller 210 to set SCU 160 in a state where it delivers a prescribed stimulation pattern, when desired, 6. When desired, patient 208 employs controller 210 to turn off SCU 160.

7. Periodically, the patient or caregiver recharges the power source/storage device 166 of SCU 160, it necessary, as described above.

For the treatment of any of the various types of sexual dysfunction, it may be desirable to modify or adjust the algorithmic functions performed by the implanted and/or external components, as well as the surgical approaches, in ways that would be obvious to skilled practitioners of these arts. For example, it may be desirable to employ more than one SCU 160, each of which could be separately controlled by means of a digital address. Multiple channels and/or multiple patterns of electrical and/or drug stimulation might thereby be programmed by the clinician and controlled by the patient in order to deal with complex or multiple dysfunctions such as may occur as a result of spinal cord injury and neurodegenerative disorders.

As another example, while it is preferable in some instances to implant electrode(s) and/or catheter discharge portion(s) epidurally, there may be patients who respond best to intradural placement of a Bion, for instance. As yet another example, in some situations it may be advisable to perform a laminectomy (i.e., surgical removal of the posterior arch of a vertebra), for instance, to implant a paddle electrode array. Laminectomy is typically performed by a neurosurgeon; implanting epidurally by slipping a small lead between two vertebrae is typically performed by an anesthesiologist.

In one preferred embodiment, SCU 160, or a group of two or more SCUs, is controlled via closed-loop operation. A need for and/or response to stimulation is sensed via SCU 160, or by an additional SCU (which may or may not be dedicated to the sensing function), or by another implanted or external device. If necessary, the sensed information is transmitted to SCU 160. Preferably, the stimulation parameters used by SCU 160 are automatically adjusted based on the sensed information. Thus, the stimulation parameters are adjusted in a closed-loop manner to provide stimulation tailored to the response to stimulation.

According to one therapeutic alternative, the dysfunction is treated by inhibiting excitement of sympathetic nerve input to the penis. Relatively high-frequency electrical stimulation (e.g., greater than about 50–100 Hz) is likely to produce such inhibition. Thus, electrodes of an SCU(s) are preferably implanted within or adjacent to one or more of the mediolateral nucleus 100, ventral root 102, and ganglion 106, in order to inhibit sympathetic input that retards erection. This inhibition may also or instead be accomplished with infusion of, for example, one or more sympathetic excitatory neurotransmitter antagonists, such as adrenergic receptor antagonists, e.g., yohimbine, into ganglion 106. Alternatively or additionally, a sympathetic inhibitory neurotransmitter agonist, such as GABA, may be infused. One or more stimulating drugs may be applied to ganglion 106, and may be (but does not need to be) combined with electrical stimulation of one or more the sympathetic sites.

According to another therapeutic alternative, the dysfunction is treated with increased excitement of the parasympathetic input to the penis. Relatively low-frequency electrical stimulation (e.g., less than about 50–100 Hz) is likely to produce such excitement. Therefore, for instance, electrical stimulation may be applied to one or more ventral roots of S1–S5.

In yet another alternative, placement of the SCU(s) is chosen to effect emission (discharge of semen) or ejaculation (ejection of semen in orgasm). While parasympathetic input is responsible for erection, sympathetic impulses are required for ejaculation. Therefore, excitatory electrical stimulation applied to one or more of the aforementioned sympathetic sites and/or excitatory drug stimulation (e.g., sympathetic excitatory neurotransmitter agonist and/or sympathetic inhibitory neurotransmitter antagonist) applied to one or more sympathetic ganglion should lead to emission and/or ejaculation. Furthermore, sensing means described earlier may be used to orchestrate first the activation of device(s) targeting nerves that cause erection, and then, when appropriate, the device(s) targeting nerves that cause ejaculation. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient with erectile dysfunction, comprising:
   providing at least one stimulator having at least two electrodes;
   implanting the at least one stimulator in or near a spinal segment responsible for erectile response;
   providing operating power to the at least one stimulator;
   providing stimulation parameters to the at least one stimulator;
   providing a sensor to sense a condition;
   using the sensed condition to adjust the stimulation parameters;
   generating stimulation pulses in accordance with the stimulation parameters; and
   delivering the stimulation pulses to nerves and tissue adjacent to the at least two electrodes;
   wherein the stimulator has a size and shape suitable for placement through a hypodermic tube or similar sized cannula, and
   wherein the stimulator has a size and shape suitable for placement in or near the spinal segment.

2. The method of claim 1 wherein the spinal segment comprises at least one of T10, T11, T12, L1, L2 L3, L4, S1, S2, S3, S4, and S5.

3. The method of claim 1 wherein the stimulation pulses comprise electrical pulses delivered at less than about 100 Hz.

4. The method of claim 3 wherein the spinal segment comprises at least one of S1, S2, S3, S4, and S5.

5. The method of claim 4 wherein the stimulator is implanted in or adjacent to the ventral root of the spinal segment.

6. The method of claim 1 wherein the stimulation pulses comprise electrical pulses delivered at greater than about 100 Hz.

7. The method of claim 6 wherein the spinal segment comprises at least one of T10, T11, T12, L1, L2, L3, and L4.

8. The method of claim 7 wherein the stimulator is implanted in or adjacent to at least one of the mediolateral column of the spinal segment, a ventral root of the spinal segment, and a sympathetic ganglion of the spinal segment.

9. The method of claim 1 wherein the sensor is independent of the stimulator.

10. The method of claim 1 wherein the sensor is provided within the stimulator.

11. A method of treating patients with erectile dysfunction, comprising:
    implanting at least one system control unit in the body of the patient, wherein the unit controls the delivery of at least one predetermined stimulus to at least ane spinal segment responsible for erectile response;
    sensing a condition and using the sensed condition to automatically determine the stimulus to apply;
    applying the at least one predetermined stimulus to at least one spinal segment, while maintaining the posterior roots of the at least one, spinal segment intact, in order to at least in part alleviate symptoms the erectile dysfunction of the patient being treated
    wherein the at least one spinal segment is selected from at least one of the spinal segments T10, T11 T12, L1, L2, L3, L4, S1, S2, S3, S4, and S5.

12. The method of claim 11 wherein the system control unit is connected to at least two electrodes, and wherein applying the at least one predetermined stimulus comprises applying electrical stimulation delivered via the at least two electrodes.

13. The method of claim 12 wherein applying electrical stimulation comprises generating and delivering stimulation pulses at less than about 100 Hz.

14. The method of claim 13 wherein the spinal segment comprises at least one of S1, S2, S3, S4, and S5 and wherein the stimulation is applied to initiate erection.

15. The method of claim 13 wherein the spinal segment comprises at least one of T10, T11, T12, L1, L2, L3, and L4 and wherein the stimulation is applied to initiate emission or ejaculation.

16. The method of claim 15 wherein one or more electrodes of the stimulator are implanted in or adjacent to at least one of the mediolateral nucleus of the spinal segment, the ventral root of the spinal segment, and a sympathetic ganglion of the spinal segment.

17. The method of claim 12 wherein applying electrical stimulation comprises generating and delivering stimulation pulses at greater than about 100 Hz.

18. The method of claim 17 wherein the spinal segment comprises at least one of T10, T11, T12, L1, L2, L3, and L4 and wherein the stimulation is applied to inhibit sympathetic input that retards erection.

19. The method of claim 18 wherein one or more electrodes of the stimulator are implanted in or adjacent to at least one of the mediolateral column of the spinal segment, a ventral root of the spinal segment, and a sympathetic ganglion of the spinal segment.

20. The method of claim 17 wherein the spinal segment comprises at least one of S1, S2, S3, S4, and S5 and wherein the stimulation is applied to inhibit parasympathetic input that retards emission and ejaculation.

21. The method of claim 11 wherein one or more electrodes of the stimulator are implanted in or adjacent to the ventral root of the spinal segment.

22. A method of treating patients with erectile dysfunction, comprising:
    implanting at least one system control unit in the body of the patent, wherein the unit controls the delivery of at least one predetermined stimulus to at least one spinal segment responsible for erectile response;
    applying the at least one predetermined stimulus to at least one spinal segment, while maintaining the posterior roots of the at least one spinal segment intact, in order to at least in part alleviate symptoms of the erectile dysfunction of the patient being treated
    wherein the at least one spinal segment is selected from at least one of the spinal segments T10, T11, T12, L1, L2, L3, L4, S1, S2, S3, S4, and S5;
    wherein the system control unit is connected to at least one catheter, and wherein applying the at least one predetermined stimulus comprises applying chemical stimulation via one or more stimulating drugs delivered through the at least one catheter.

23. The method of claim 22 wherein the distal end of the at least one catheter is applied to a sympathetic ganglia of the at least one spinal segment end wherein the stimulating drug is applied to inhibit sympathetic input that retards erection.

24. The method of claim 23 wherein the stimulating drug comprises one or more of an adrenergic receptor antagonist and a GABA agonist.

25. The method of claim 22 wherein the distal end of the at least one catheter is applied to a sympathetic ganglia of the at least one spinal segment and wherein the stimulating drug is applied to excite sympathetic input that initiates emission or ejaculation.

26. The method of claim 25 wherein the stimulating drug comprises one or more of an adrenergic receptor agonist and a GABA antagonist.

27. The method of claim 22 wherein the system control unit is connected to at least two electrodes and to the at least one catheter, and wherein applying the at least one predetermined stimulus comprises applying both electrical stimulation delivered via the at least two electrodes and chemical stimulation via one or more stimulating drugs delivered through the at least one catheter.

28. A method of treating patients with erectile dysfunction, comprising:
    implanting at least one system control unit in the body of the patient, wherein the unit controls the delivery of at least one predetermined stimulus to at least one spinal segment responsible for erectile response;
    sensing a condition and using the sensed condition to automatically determine the stimulus to apply;
    applying the at least one predetermined stimulus through the dura to at least one spinal segment in order to at least part alleviate symptoms of the erectile dysfunction of the patient being treated
    wherein the at least one spinal segment is selected form at least one of the spinal segments T10, T11, T12, L1, L2, L3, L4, S1, S2, S3, S4, and S5.

29. The method of claim 28 wherein the system control unit is connected to at least two electrodes, and wherein applying the at least one predetermined stimulus comprises applying electrical stimulation delivered via the at least two electrodes.

30. The method of claim 29 wherein applying electrical stimulation comprises generating and delivering stimulation pulses at less than about 100 Hz.

31. The method or claim 30 wherein the spinal segment comprises at least one of S1, S2, S3, S4, and S5 and wherein the stimulation is applied to initiate erection.

32. The method of claim 30 wherein the spinal segment comprises at least one of T10, T11, T12, L1, L2, L3, and L4 and wherein the stimulation is applied to initiate emission or ejaculation.

33. The method of claim 32 wherein one or more electrodes of the stimulator are implanted in or adjacent to at least one of the mediolateral nucleus of the spinal segment, the ventral root of the spinal segment, and a sympathetic ganglion of the spinal segment.

34. The method of claim 29 wherein applying electrical stimulation comprises generating and delivering stimulation pulses at greater than about 100 Hz.

35. The method of claim 34 wherein the spinal segment comprises at least one of T10, T11, T12, L1, L2, L3, and L4 and wherein the stimulation is applied to inhibit sympathetic input that retards erection.

36. The method of claim 35 wherein one or more electrodes of the stimulator are implanted in or adjacent to at least one of the mediolateral column of the spinal segment, a ventral root of the spinal segment, and a sympathetic ganglion of the spinal segment.

37. The method of claim 34 wherein the spinal segment comprises at least one of S1, S2, S3, S4, and S5 and wherein the stimulation is applied to inhibit parasympathetic input that retards emission and ejaculation.

38. The method of claim 28 wherein one or more electrodes of the stimulator are implanted adjacent to the ventral root of the spinal segment.

39. A method of treating patients with erectile dysfunction, comprising:
    implanting at least one system control unit in the body of the patient, wherein the unit controls the delivery of at least one predetermined stimulus to at least one spinal segment responsible for erectile response;
    applying the at least one predetermined stimulus through the dura to at least one spinal segment in order to at least in part alleviate symptoms of the erectile dysfunction of the patient being treated wherein the at least one spinal segment is selected from at least one of the spinal segments T10, T11, T12, L1, L2, L3, L4, S1, S2, S3, S4, and S5;

wherein the system control unit is connected to at least one catheter, and wherein applying the at least ore predetermined stimulus comprises applying chemical stimulation via one or more stimulating drugs delivered through the at least one catheter.

40. The method of claim 39 wherein the distal end of the at least one catheter is applied to a sympathetic ganglia of the at least one spinal segment and wherein the stimulating drug is applied to inhibit sympathetic input that retards erection.

41. The method of claim 40 wherein the stimulating drug comprises one or more of an adrenergic receptor antagonist and a GABA agonist.

42. The method of claim 39 wherein the distal end of the at least one catheter is applied to a sympathetic ganglia of the at least one spinal segment and wherein the stimulating drug is applied to excite sympathetic input that initiates emission or ejaculation.

43. The method of claim 42 wherein the stimulating drug comprises one or more of an adrenergic receptor agonist and a GABA antagonist.

44. The method of claim 39 wherein the system control unit is connected to at least two electrodes and to the at least one catheter, and wherein applying the at least one predetermined stimulus comprises applying both electrical stimulation delivered via the at least two electrodes and chemical simulation via one or more stimulating drugs delivered through the at least one catheter.

* * * * *